(12) United States Patent
Messerli et al.

(10) Patent No.: US 7,601,173 B2
(45) Date of Patent: Oct. 13, 2009

(54) MULTIPIECE ALLOGRAFT IMPLANT

(75) Inventors: Dominique Messerli, Downington, PA (US); Jacqueline Myer, Pottstown, PA (US); Michael L. Boyer, II, Malvern, PA (US); Christopher H. Angelucci, Schwenkesville, PA (US)

(73) Assignee: Synthes USA, LLC, West Chester, PA (US)

( * ) Notice: Subject to any disclaimer, the term of this patent is extended or adjusted under 35 U.S.C. 154(b) by 228 days.

(21) Appl. No.: 11/745,343

(22) Filed: May 7, 2007

(65) Prior Publication Data

US 2007/0208424 A1    Sep. 6, 2007

Related U.S. Application Data

(63) Continuation of application No. 10/931,788, filed on Sep. 1, 2004, now Pat. No. 7,226,482.

(60) Provisional application No. 60/449,926, filed on Sep. 2, 2003.

(51) Int. Cl.
*A61F 2/44*    (2006.01)

(52) U.S. Cl. .............. 623/17.11; 623/17.16; 623/23.51; 606/246

(58) Field of Classification Search ................. 606/246; 623/23.51, 17.11–17.16
See application file for complete search history.

(56) References Cited

U.S. PATENT DOCUMENTS

| | | | |
|---|---|---|---|
| 2,621,145 A | 12/1952 | Sano | 167/84 |
| 4,135,506 A | 1/1979 | Ulrich | 128/92 B |
| 4,501,269 A | 2/1985 | Bagby | 128/92 G |
| 4,512,038 A | 4/1985 | Alexander et al. | 3/1.9 |
| 4,627,853 A | 12/1986 | Campbell et al. | |
| 4,678,470 A | 7/1987 | Nashef et al. | 623/16 |
| 4,717,115 A | 1/1988 | Schmitz | |
| 4,858,603 A | 8/1989 | Clemow et al. | 128/92 ZW |
| 4,936,851 A | 6/1990 | Fox et al. | |
| 4,950,296 A | 8/1990 | McIntyre | 623/16 |
| 4,961,740 A | 10/1990 | Ray et al. | 606/61 |
| 4,994,084 A | 2/1991 | Brennan | 623/11 |
| 5,026,373 A | 6/1991 | Ray et al. | 606/61 |
| 5,053,049 A | 10/1991 | Campbell | |
| 5,062,850 A | 11/1991 | MacMillan et al. | 623/17 |
| 5,084,051 A | 1/1992 | Törmälä et al. | 606/77 |
| 5,112,354 A | 5/1992 | Sires | 623/16 |
| 5,192,327 A | 3/1993 | Brantigan | 623/17 |
| 5,211,664 A | 5/1993 | Tepic et al. | |
| 5,281,226 A | 1/1994 | Davydov et al. | 606/62 |
| 5,284,655 A | 2/1994 | Bogdansky et al. | 424/422 |

(Continued)

FOREIGN PATENT DOCUMENTS

DE    30 42 003 A1    7/1982

(Continued)

*Primary Examiner*—David H Willse
*Assistant Examiner*—Javier G Blanco
(74) *Attorney, Agent, or Firm*—Stroock & Stroock & Lavan LLP

(57) ABSTRACT

An allogenic implant for use in intervertebral fusion is formed from two parts. The first part, composed of cortical bone, provides mechanical strength to the implant, allowing the proper distance between the vertebrae being treated to be maintained. The second part, composed of cancellous bone, is ductile and promotes the growth of new bone between the vertebrae being treated and the implant, thus fusing the vertebrae to the implant and to each other. The implant is sized and shaped to conform to the space between the vertebrae. Teeth formed on the superior and inferior surfaces of the implant prevent short-term slippage of the implant.

18 Claims, 6 Drawing Sheets

U.S. PATENT DOCUMENTS

| | | | |
|---|---|---|---|
| 5,298,254 A | 3/1994 | Prewett et al. | 424/422 |
| 5,314,476 A | 5/1994 | Prewett et al. | 623/16 |
| 5,348,788 A | 9/1994 | White | |
| 5,405,391 A | 4/1995 | Hednerson et al. | 623/17 |
| 5,423,817 A | 6/1995 | Lin | 606/61 |
| 5,439,684 A | 8/1995 | Prewett et al. | 424/422 |
| 5,458,638 A | 10/1995 | Kuslich et al. | 623/17 |
| 5,489,308 A | 2/1996 | Kuslich et al. | 623/17 |
| 5,507,818 A | 4/1996 | McLaughlin | 623/18 |
| 5,514,180 A | 5/1996 | Heggeness et al. | 623/17 |
| 5,522,899 A | 6/1996 | Michelson | 623/17 |
| 5,534,030 A | 7/1996 | Navarro et al. | 623/17 |
| 5,549,679 A | 8/1996 | Kuslich | 623/17 |
| 5,554,191 A | 9/1996 | Lahille et al. | 623/17 |
| 5,556,430 A | 9/1996 | Gendler | 623/16 |
| 5,569,308 A | 10/1996 | Sottosanti | 623/165 |
| 5,571,190 A | 11/1996 | Ulrich et al. | 623/17 |
| 5,571,192 A | 11/1996 | Schönhöffer | 623/17 |
| 5,607,474 A | 3/1997 | Athanasiou et al. | 623/11 |
| 5,609,635 A | 3/1997 | Michelson | 623/17 |
| 5,609,636 A | 3/1997 | Kohrs et al. | 623/17 |
| 5,609,637 A | 3/1997 | Biedermann et al. | 623/17 |
| 5,676,699 A | 10/1997 | Gogolewski et al. | |
| 5,683,394 A | 11/1997 | Rinner | 606/86 |
| 5,683,463 A | 11/1997 | Godefroy et al. | 623/17 |
| 5,702,449 A | 12/1997 | McKay | 623/17 |
| 5,702,451 A | 12/1997 | Biedermann et al. | 623/17 |
| 5,702,453 A | 12/1997 | Rabbe et al. | 623/17 |
| 5,702,455 A | 12/1997 | Saggar | 623/17 |
| 5,728,159 A | 3/1998 | Stroever et al. | 623/16 |
| 5,735,905 A | 4/1998 | Parr | 623/23 |
| 5,766,253 A | 6/1998 | Brosnahan, III | 623/17 |
| 5,776,197 A | 7/1998 | Rabbe et al. | 623/17 |
| 5,776,198 A | 7/1998 | Rabbe et al. | 623/17 |
| 5,776,199 A | 7/1998 | Michelson | 623/17 |
| 5,782,915 A | 7/1998 | Stone | 623/11 |
| 5,785,710 A | 7/1998 | Michelson | 606/61 |
| 5,865,849 A | 2/1999 | Stone | 623/18 |
| 5,876,452 A | 3/1999 | Athanasiou et al. | 623/16 |
| 5,885,299 A | 3/1999 | Winslow et al. | 606/99 |
| 5,888,222 A | 3/1999 | Coates et al. | 623/17 |
| 5,888,224 A | 3/1999 | Beckers et al. | 623/17 |
| 5,888,227 A | 3/1999 | Cottle | 623/17 |
| 5,895,426 A | 4/1999 | Scarborough et al. | 623/17 |
| 5,899,939 A | 5/1999 | Boyce et al. | 623/16 |
| 5,902,338 A | 5/1999 | Stone | 623/13 |
| 5,904,719 A | 5/1999 | Errico et al. | 623/17 |
| 5,910,315 A | 6/1999 | Stevenson et al. | 424/422 |
| 5,922,027 A | 7/1999 | Stone | 623/11 |
| 5,944,755 A | 8/1999 | Stone | 623/16 |
| 5,968,098 A | 10/1999 | Winslow | 623/17 |
| 5,972,368 A | 10/1999 | McKay | 424/423 |
| 5,976,187 A | 11/1999 | Richelsoph | 623/17 |
| 5,980,522 A | 11/1999 | Koros et al. | 606/61 |
| 5,981,828 A | 11/1999 | Nelson et al. | 623/16 |
| 5,984,967 A | 11/1999 | Zdeblick et al. | 623/17 |
| 5,989,289 A | 11/1999 | Coates et al. | 623/17 |
| 6,013,853 A | 1/2000 | Athanasiou et al. | 623/11 |
| 6,025,538 A | 2/2000 | Yaccarino, III | 623/16 |
| 6,033,405 A | 3/2000 | Winslow et al. | 606/61 |
| 6,033,438 A | 3/2000 | Bianchi et al. | 623/17 |
| 6,039,762 A | 3/2000 | McKay | 623/17 |
| 6,045,579 A | 4/2000 | Hochshuler et al. | 623/17 |
| 6,045,580 A | 4/2000 | Scarborough et al. | 623/17 |
| 6,080,158 A | 6/2000 | Lin | 606/61 |
| 6,080,193 A | 6/2000 | Hochshuler et al. | 623/17 |
| 6,090,998 A | 7/2000 | Grooms et al. | 623/16 |
| 6,096,081 A | 8/2000 | Grivas et al. | 623/17.11 |
| 6,110,482 A | 8/2000 | Khouri et al. | 424/423 |
| 6,123,731 A | 9/2000 | Boyce et al. | 623/23.63 |
| 6,129,763 A | 10/2000 | Chauvin et al. | 623/17 |
| 6,143,030 A | 11/2000 | Schroder | 623/16.11 |
| 6,143,033 A | 11/2000 | Paul et al. | 623/17.11 |
| 6,156,070 A | 12/2000 | Incavo et al. | 623/23.52 |
| 6,193,756 B1 | 2/2001 | Studer et al. | 623/17.15 |
| 6,200,347 B1 | 3/2001 | Anderson et al. | 623/16.11 |
| 6,241,769 B1 | 6/2001 | Nicholson et al. | 623/17.11 |
| 6,245,108 B1 | 6/2001 | Biscup | 623/17.11 |
| 6,258,125 B1 | 7/2001 | Paul et al. | 623/17.11 |
| 6,261,586 B1 | 7/2001 | McKay | |
| 6,264,695 B1 | 7/2001 | Stoy | 623/17.16 |
| 6,270,528 B1 | 8/2001 | McKay | |
| 6,458,158 B1 | 10/2002 | Anderson et al. | 623/16.11 |
| 6,468,311 B2 | 10/2002 | Boyd et al. | |
| 6,569,201 B2 | 5/2003 | Moumene et al. | |
| 6,638,310 B2 | 10/2003 | Lin et al. | |
| 6,761,738 B1 | 7/2004 | Boyd et al. | |
| 6,761,739 B2 | 7/2004 | Shepard | 623/17.16 |
| 2001/0001129 A1 | 5/2001 | McKay et al. | 623/17.16 |
| 2001/0010021 A1 | 7/2001 | Boyd et al. | 623/17.13 |
| 2001/0016777 A1 | 8/2001 | Biscup | 623/17.16 |
| 2001/0031254 A1 | 10/2001 | Bianchi et al. | |
| 2001/0032017 A1 | 10/2001 | Alfaro et al. | |
| 2001/0039456 A1 | 11/2001 | Boyer, II et al. | 623/23.52 |
| 2001/0041941 A1 | 11/2001 | Boyer, II et al. | 623/23.52 |
| 2002/0029084 A1 | 3/2002 | Paul et al. | 623/23.63 |
| 2002/0091447 A1 | 7/2002 | Shimp et al. | 623/17.16 |
| 2002/0106393 A1 | 8/2002 | Bianchi et al. | 424/423 |
| 2004/0078078 A1 | 4/2004 | Shepard | 623/17.11 |

FOREIGN PATENT DOCUMENTS

| | | |
|---|---|---|
| DE | 39 33 459 A1 | 4/1991 |
| DE | 42 42 889 A1 | 6/1994 |
| DE | 44 09 392 A1 | 9/1995 |
| DE | 44 23 257 A1 | 11/1996 |
| DE | 195 04 867 C1 | 12/1997 |
| DE | 299 13 200 U1 | 10/1999 |
| EP | 0505634 | 9/1992 |
| EP | 0517030 | 12/1992 |
| EP | 0 577 178 A1 | 1/1994 |
| EP | 0 639 351 A2 | 11/1996 |
| EP | 0 966 930 | 12/1999 |
| EP | 0 968 692 A1 | 1/2000 |
| FR | 2 552 659 | 4/1985 |
| FR | 2 700 947 | 8/1994 |
| FR | 2 697 996 | 9/1995 |
| FR | 2 753 368 | 10/2000 |
| GB | 2 148 122 A | 5/1985 |
| SU | 1465040 A1 | 3/1989 |
| WO | WO 88/03417 | 5/1988 |
| WO | WO 88/10100 | 12/1988 |
| WO | WO 92/01428 | 2/1992 |
| WO | WO 9521053 | 8/1995 |
| WO | WO 96/39988 | 12/1996 |
| WO | WO 97/20526 | 6/1997 |
| WO | WO 97/25941 | 7/1997 |
| WO | WO 97/25945 | 7/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/29271 | 6/1999 |
| WO | WO 99/32055 | 7/1999 |
| WO | WO 99/38461 | 8/1999 |
| WO | WO 99/56675 | 11/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/74607 A1 | 12/2000 |

MULTIPIECE ALLOGRAFT IMPLANT

CROSS REFERENCE TO RELATED APPLICATION

This application is a continuation of prior patent application Ser. No. 10/931,788, filed Sep. 1, 2004, now U.S. Pat. No. 7,226,482 B2, which claims priority from U.S. provisional patent application No. 60/499,926, filed Sep. 2, 2003. The entire contents of these applications are expressly incorporated herein by reference thereto

FIELD OF THE INVENTION

The present invention is directed to an allogenic implant and, more particularly, to an allogenic intervertebral implant for the fusion of vertebrae.

BACKGROUND OF THE INVENTION

A number of medical conditions, such as compression of spinal cord nerve roots, degenerative disc disease, and trauma can cause severe back pain. Intervertebral fusion is a surgical method of alleviating back pain. In intervertebral fusion, two adjacent vertebral bodies are fused together by removing the affected intervertebral disc and inserting an implant that would allow for bone to grow between the two vertebral bodies to bridge the gap left by the removed disc.

A number of different implants and implant materials have been used for fusion with varying success. Current implants for intevertebral fusion include metallic cages and allografts. Metallic cages suffer from the disadvantage of requiring drilling and tapping of the vertebral endplates for insertion. In addition, the incidence of subsidence in long term use is not known. Due to MRI incompatibility of metallic cages, determining fusion is problematic.

Allografts are sections of bone taken from the diaphysis of a long bone, such as the radius, ulna, fibula, humerus, tibia, or femur of a donor. A cross-section of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They also promote the formation of bone, i.e., osteoconductive, and are also MRI compatible so that fusion can be more accurately ascertained. Although the osteoconductive nature of the allograft provides a biological interlocking between the allograft and the vertebrae for long term mechanical strength, initial and short term mechanical strength of the interface between the allograft and the vertebrae needs to be addressed to minimize the possibility of the allograft being expelled after implantation.

Most allografts are simply sections of bone which, although cut to the approximate height of the disc being replaced, have not been sized and/or machined on the exterior surface to have a uniform shape. As a result, the fusion of the vertebral bodies does not occur in optimal anatomic position or in a consistent manner along the surface of the endplates. While a surgeon may do some minimal intraoperative shaping and sizing to customize the allograft for the patient's spinal anatomy, significant shaping and sizing of the allograft during the procedure is not possible due to the nature of the allograft. Even if extensive shaping and sizing were possible, a surgeon's ability to manually shape and size the allograft to the desired dimensions is limited.

With respect to the overall structure of a given bone, the mechanical properties vary throughout the bone. For example, a long bone (leg bone) such as the femur has both cortical bone and cancellous bone. Cortical bone, the compact and dense bone that surrounds the marrow cavity, is generally solid and thus carries the majority of the load in long bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10-20 MPa and a density of about 0.7, cortical bone has a tensile strength of about 100-200 MPa and a density of about 2. Additionally, the strain to failure of cancellous bone is about 5-7%, while cortical bone can only withstand 1-3% strain before failure. It should also be noted that these mechanical characteristics may degrade as a result of numerous factors such as any chemical treatment applied to the bone material, and the manner of storage after harvesting but prior to implantation (i.e. drying of bones).

Notably, implants of cancellous bone incorporate more readily with the surrounding host bone, due to the superior osteoconductive nature of cancellous bone as compared to cortical bone. Furthermore, cancellous bone from different regions of the body is known to have a range of porosities. Thus, the design of an implant using cancellous bone may be tailored to specifically incorporate material of a desired porosity.

There is a need for an allograft that properly utilizes the different properties of cortical and cancellous bone to improve stability and to promote growth of new bone to fuse the vertebrae being treated during intervertebral fusion.

SUMMARY OF THE INVENTION

The present invention relates to an allogenic intervertebral implant for use when surgical fusion of vertebral bodies is indicated. The implant preferably comprises a wedge or plug conforming in size and shape with the end plates of adjacent vertebrae and has a plurality of teeth positioned on the top and bottom surfaces for interlocking with the adjacent vertebrae. The teeth preferably have a pyramid shape or a saw-tooth shape.

The implant preferably is comprised of two or more parts. At least the first part is preferably composed of cortical bone, while at least the second part is preferably composed of cancellous bone. The implant is configured so that when inserted between the vertebrae to be treated, the cortical and cancellous parts of the allograft are positioned so that the different properties possessed by the cortical and cancellous bone may be utilized effectively. The cortical part of the allograft is aligned with the vertebrae so that it bears the majority of the forces exerted on the implant, while the cancellous bone section promotes the growth of new bone with the implant to allow the vertebrae being treated to fuse with the allograft and each other.

The two or more sections preferably are attached by a dovetail joint. One or more pins may also be used to prevent the two sections from sliding out of connection with each other. The pins may be made of allogenic bone. Preferably the two or more pieces or sections are aligned so that they are side by side when inserted between vertebrae.

The implant preferably has teeth that are formed at least in the cortical section of the allograft. Teeth formed from cortical bone, being much harder and stiffer than cancellous bone, are more effective in keeping the implant from being displaced. Furthermore, since the cortical part of the implant is where most of the load bearing occurs, teeth formed in this part have the greatest ability to grip into the vertebrae surfaces. Teeth may also be formed in portions of or the entire cancellous bone section or sections.

The implant may take on various profiles and exterior geometries, depending upon the area of the spine that is to be treated. The implant may further be shaped with various thicknesses, to maintain the proper distance between the vertebrae being treated.

DESCRIPTION OF THE PREFERRED EMBODIMENTS

Figure 1:
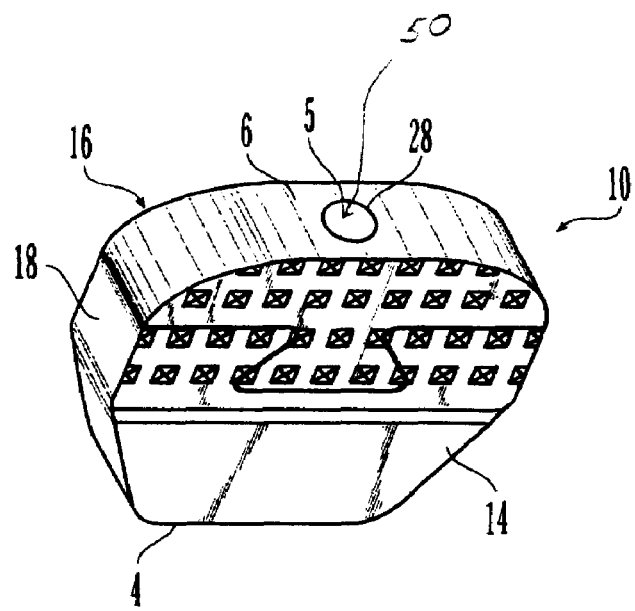
FIG. 1 is a perspective view of an exemplary embodiment of the implant according to the present invention.
Figure 2:
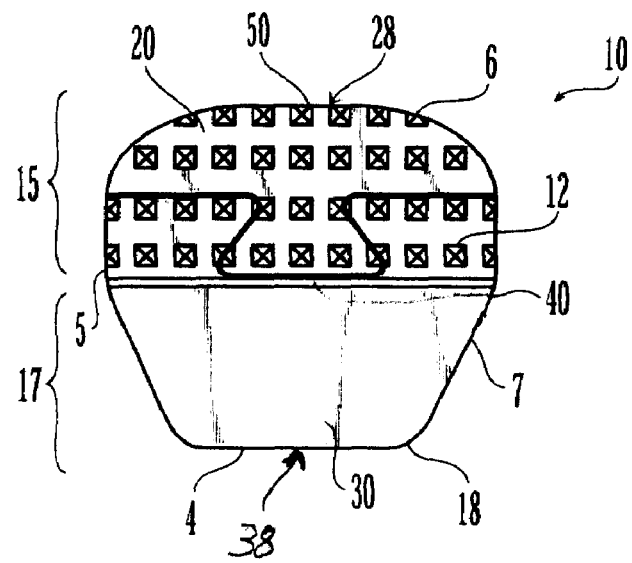
FIG. 2 is a top view of the embodiment of FIG. 1.
Figure 3:
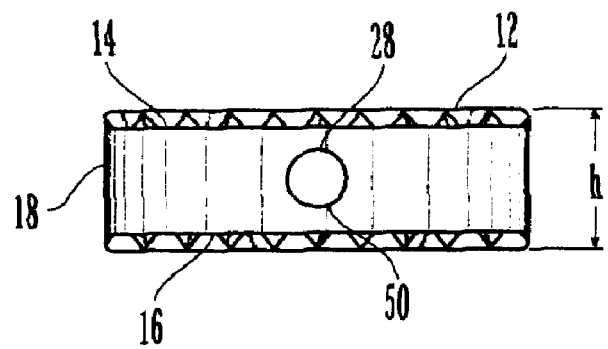
FIG. 3 is a back view of the embodiment of FIG. 1.

FIG. 1 shows a perspective view of a first embodiment of an intervertebral allograft spacer or implant 10 according to the present invention. Implant 10 preferably is shaped to conform in size and shape with at least a portion of the end plates of the vertebrae between which implant 10 is to be used. The outer periphery of implant 10 may be sided and shaped to match the outer periphery of the end plates of the vertebrae between which the implant 10 is to be used. Alternatively the outer periphery of the implant 10 may be sided and shaped to match only a portion of the outer periphery of the end plates of the vertebrae, or it may have an outer periphery that may not match the peripheral shape of the end plates of the vertebrae at any location.

Implant 10 generally comprises a superior surface 14, an inferior surface 16, and an exterior surface 18. Superior surface 14 and inferior surface 16 further may comprise toothed sections 15 and flat sections 17. Toothed sections 15 of superior surface 14 and inferior surface 16 may be generally of the same size and shape, with toothed sections 15 being formed towards anterior end 6 and flat sections 17 being formed towards posterior end 4.

Figure 4:
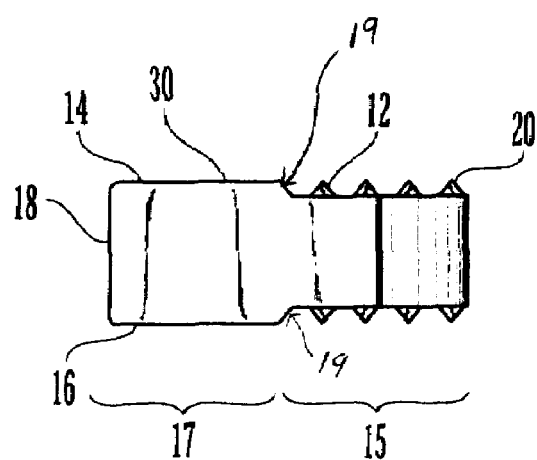
FIG. 4 is a side view of the embodiment of FIG. 1.

Implant 10 preferably is formed by the connection of first part 20 and second part 30. First part 20 preferably is formed from cortical bone. Second part 30 preferably is composed of cancellous bone. First part 20 and second part 30 preferably are connected by a dovetail joint 40 so that first part 20 and second part 30 are connected side by side to each other. Second part 30 may comprise a ledge 19 (see FIG. 4) between a flat section and a toothed section of both superior surface 14 and inferior surface 16. First part 20 and second part 30 may further comprise first hole 28 and first hole 38 (not shown) through which pin 50 may be inserted to prevent sliding of first part 20 and second part 30 along dovetail joint 40. First hole 28 may be formed such that it goes through the entire length of first part 20. Second hole 38 may be formed such that it goes through the entire length of second part 30 or only a portion thereof. Pin 50 may be inserted through the entirety of first part 20 and second part 30 or through only a portion thereof. Pin 50 may be sized such that pin 50 protrudes from either first hole 28 or second hole 38 when pin is fully inserted. In this case, any excess portion of pin 50 protruding from first hole 28 or second hole 38 may be removed by further processing. Alternatively, pin may be sized so that it does not extend all the way through both first hole 28 and/or second hole 38.

Figure 7:
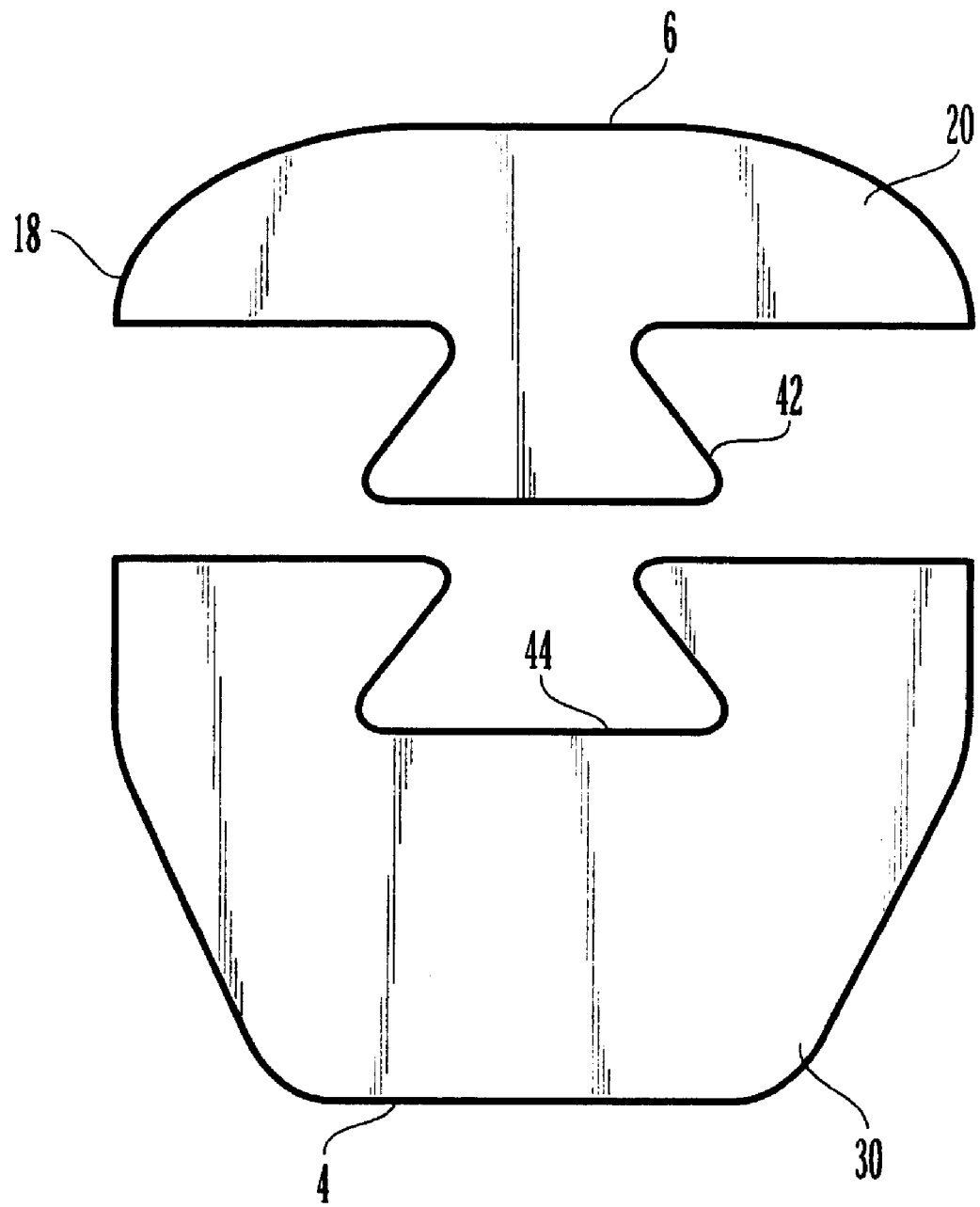
FIG. 7 is a top exploded view of the implant of FIG. 1.

As shown in FIG. 7, male portion 42 of dovetail joint 40 may be formed on first part 20, and female portion 44 of dovetail joint 40 may be formed on second part 30. However, in an alternative embodiment, male portion 42 may be formed on second part 30 and female portion 44 may be formed on first part 20. Male portion 42 may have a length z that preferably is approximately 3 mm, a first width x at its narrowest point that preferably is approximately 3.1 mm, and a second width y at its widest point that preferably is approximately 6.3 mm, with female portion 44 having corresponding dimensions (see FIG. 13). In an alternative embodiment, female portion 44 has dimensions that are slightly smaller than the dimensions of male portion 42, thus creating an interference fit between male portion 42 and female portion 44. However, it is to be understood that male portion 42 and female portion 44 may have different dimensions than the ones described above without departing from the spirit and scope of the invention. In addition, more than one dovetail connection, and/or more than one pin connection may be used in forming implant 10. Furthermore, the pin may be inserted in alternative locations. Furthermore, other methods of connecting first part 20 and second part 30 may be used without departing from the spirit and scope of the invention.

Figure 5:
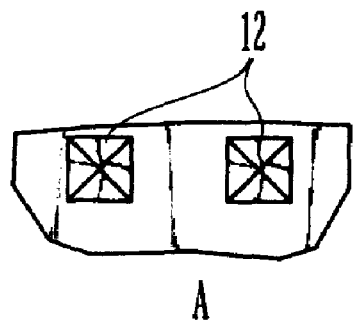
FIG. 5 is a partial top view of the embodiment of FIG. 1.
Figure 6:
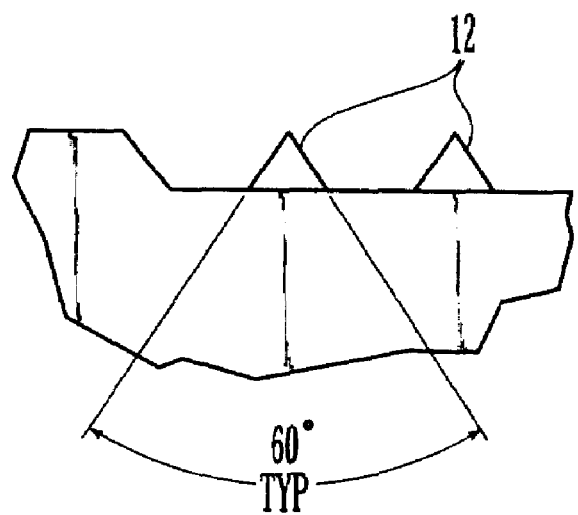
FIG. 6 is a partial side view of the embodiment of FIG. 1.
Figure 12:
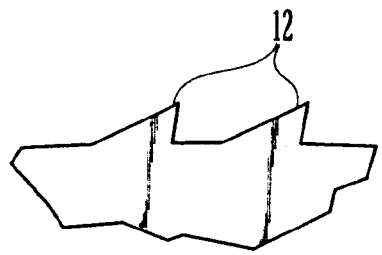
FIG. 12 is a partial side view of an alternative teeth formation for the implant of FIGS. 7, 8, and 10.

Implant 10 has a plurality of teeth 12 formed within toothed sections 14, 16 that preferably provide a mechanical interlock between implant 10 and the end plates of the vertebrae to be treated. Preferably, as shown in FIGS. 5 and 6, teeth 12 may be pyramid shaped, with the angle formed from the tip to the base being approximately 60 degrees. Alternatively, teeth 12 may have a saw tooth shape with the saw tooth running in the anterior-posterior direction (see FIG. 12).

As seen in FIGS. 1 to 4, the majority of toothed sections 15 are comprised of the entire superior surface 14 and inferior surface 16 of first part 20. Because these teeth 12 are preferably formed from cortical bone, teeth 12 have sufficient strength and hardness to impale themselves into the vertebrae surfaces and provide an enhanced interlock with the adjacent vertebrae. Teeth 12 may also be formed in second part 30 in order to simplify the manufacturing process (further described below), although these teeth 12 do not have the same strength and hardness of teeth 12 formed in first part 20.

Teeth 12 are generally arranged in a two-dimensional array or pattern. In a preferred embodiment, teeth 12 are arranged in an array composed of evenly spaced rows and columns. However, it can be readily seen by those skilled in the art that teeth 12 may be arranged within toothed sections 15 in many different ways, without departing from the spirit and scope of the present invention.

Flat sections 17 preferably are comprised entirely upon superior surface 14 and inferior surface 16 of second part 30. Flat sections 17, being formed of cancellous bone, are more ductile that toothed sections 15 and will deform to conform to the surface contours of the vertebrae being treated. This further ensures an optimal fit of implant 10 between the vertebrae and promotes fusion of the vertebrae with the implant 10, without excessive contouring of the surfaces of implant 10.

Ideally, an intervertebral implant comprises as much cancellous bone as possible while providing sufficient support to maintain the proper spacing between the vertebrae being treated, so that the promotion of new bone growth is maximized. By properly sizing and shaping first section 20 of implant 10, composed of cortical bone, and by properly aligning first part 20 so that it is subject to the majority of forces exerted on implant 10 by the vertebrae being treated, implant 10 has sufficient strength to maintain the proper distance between the vertebrae, while minimizing the amount of cortical bone required. The rest of implant 10, being composed of cancellous bone (i.e., second part 30), can then be used more advantageously to promote the growth of new bone between the vertebrae being treated, thus providing long-term stability to the vertebrae and implant 10. Because most of the load bearing of implant 10 occurs on first part 20, the effectiveness of teeth 12 formed in first part 20 to grip into the surfaces of the vertebrae is enhanced. The application of force on first part 20, and therefore teeth 12, enhances the ability of teeth 12 to penetrate into and grip the vertebrae surfaces, thus preventing short-term slippage of implant 10 until implant 10 is fused with the vertebrae by the growth of new bone.

Thus, implant 10 takes advantage of the different properties of cortical and cancellous bone to improve the use of allogenic bone in the surgical method of intervertebral fusion. Implant 10 may be customized according to the needs of the user, as different combinations of cortical and cancellous bone, may be selected, depending upon the properties desired. An implant 10 in accordance with the present invention also allows for more efficient use of available material, as pieces of allogenic bone that would otherwise not be large enough to form a suitably sized implant may be used instead to form a part of implant 10.

Figure 10:
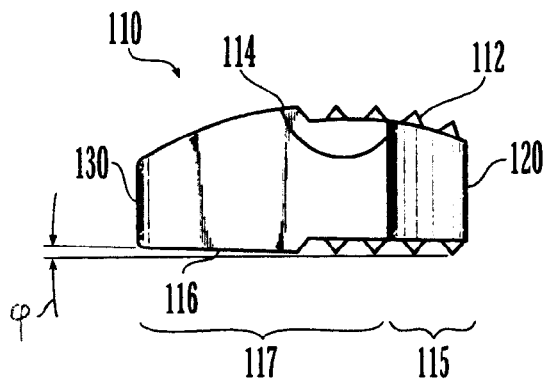
FIG. 10 is a side view of a third exemplary embodiment of an implant in accordance with the present invention.
Figure 11:
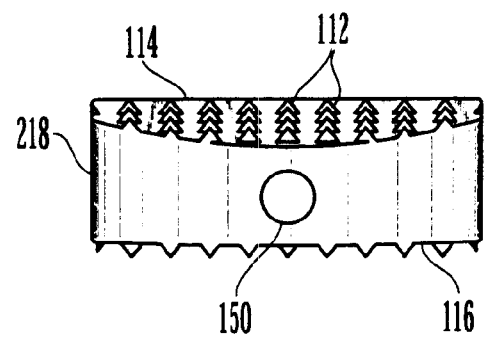
FIG. 11 is a back view of the embodiment of FIG. 1.
Figure 8:
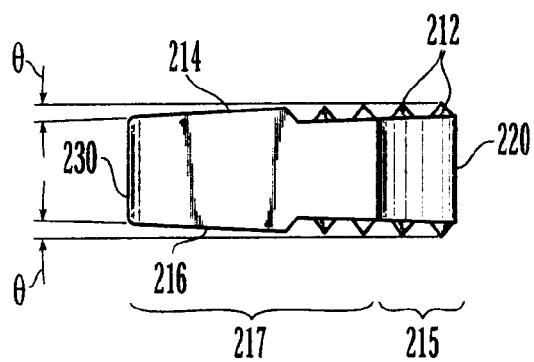
FIG. 8 is a side view of a second exemplary embodiment of an implant in accordance with the present invention.
Figure 9:
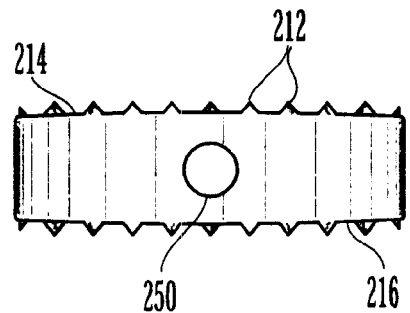
FIG. 9 is a back view of the embodiment of FIG. 8.

In the preferred embodiment shown in FIGS. 1 to 4, superior surface 14 and inferior surface 16 are parallel with each other. However, in certain areas of the spine, it may be desirable for implant 10 to have inclined and/or curved surfaces in order to restore the natural curvature of the spine after the affected disc has been removed. For example, as shown in FIGS. 8 and 9, implant 220 may have a wedge shaped profile, with superior surface 214 and inferior surface 216 each defining an angle θ. Angle θ may preferably be within the range of about 2 to about 5 degrees, and preferably is about 3.5 degrees. In yet another embodiment, as shown in FIGS. 10 and 11, inferior surface 116 defines an angle φ, while superior surface 114 is curved to conform to the surface of the topography of the vertebral end plates. Angle φ may preferably be within the range of about 2 to about 5 degrees, and preferably is about 3.5 degrees. The radius of curvature of superior surface 114 may be within the range of about 8 to about 25 mm, and preferably is about 14 mm.

Figure 13:
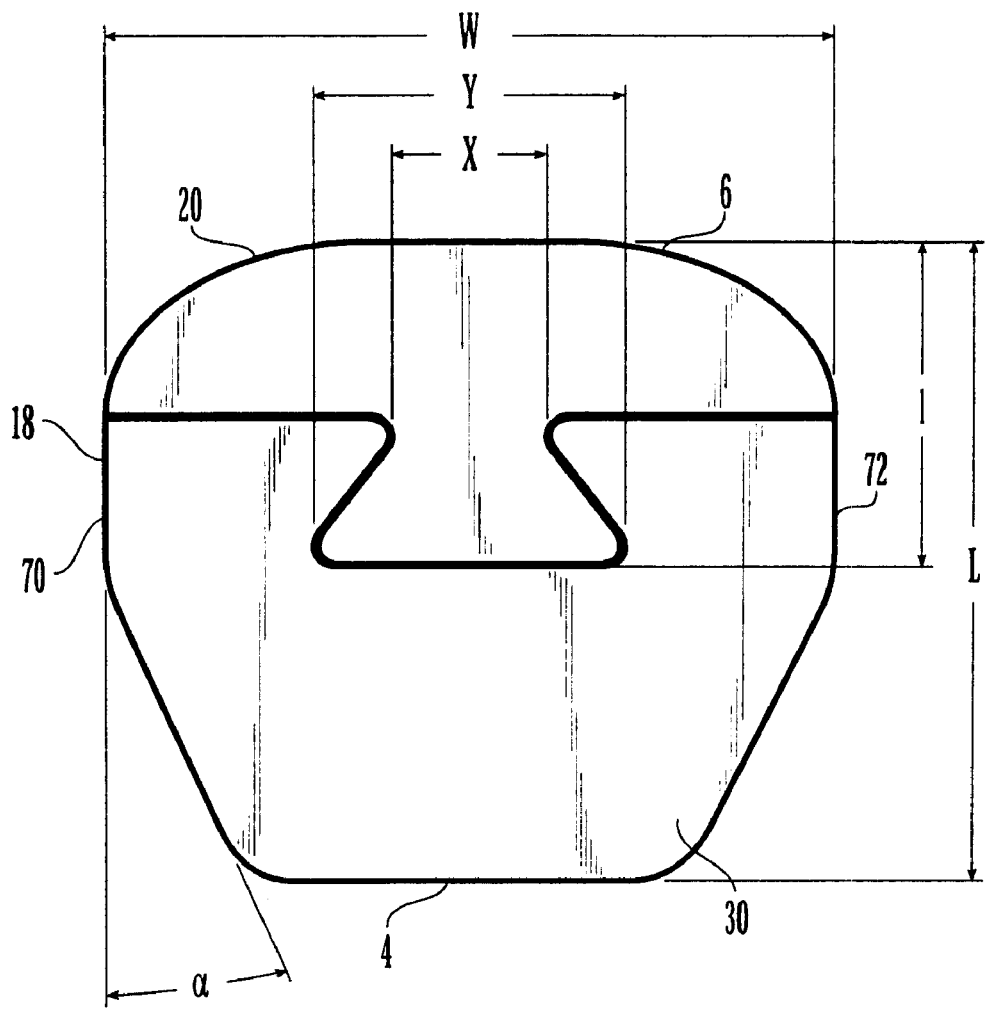
FIG. 13 is a top view showing representative dimensions of the embodiment of FIGS. 1, 8, and 10.

In the above illustrated embodiments, and as further illustrated in FIG. 13, exterior surface 18 is formed so that posterior end 4 is flat, while anterior end 6 is curved. Anterior end 6 has a radius of curvature preferably within the range of about 15 to about 25 mm, and preferably is about 20 mm. The length L of implant 10 from anterior end 6 to posterior end 4 is preferably within the range of about 10 to about 15 mm, and preferably is about 12.5 mm. First part 20 has a length l (including male section 42) preferably within the range of about 4 to about 8 mm, and preferably is about 6 mm. The width W of implant 10 from the medial surface 70 to the lateral surface 72 at its widest point is preferably within the range of about 10 to about 18 mm, and preferably is about 15 mm. Furthermore, sides 5 of exterior surface 18 that correspond with toothed sections 15 are parallel to each other, while sides 7 of exterior surface 18 that correspond with flat sections 17 are angled in towards posterior end 4 at angle α. Angle α is preferably within the range of about 20 to about 40 degrees, and preferably is about 30 degrees. With this geometry, implant 10 may ideally be used between cervical vertebrae. However, it can be readily seen by those skilled in the art that exterior surface 18 may take on many different geometries to optimize the use of implant 10 between vertebrae in different areas of the spine.

Implant 10 is manufactured by first roughly shaping first part 20 and second part 30 out of cortical and cancellous allogenic bone. Male portion 42 and female portion 44 of dovetail joint 40 are then formed in first part 20 and second part 30 respectively. Holes 28 and 38 for pin 50 are also formed in first part 20 and second part 30. Male portion 42 is then inserted in female portion 44, and pin 50 is inserted through holes 28 and 38. If desired, adhesive may be used between first part 20 and second part 30. In a preferred embodiment, pin 50 is sized so that there is a slight interference between the exterior surface of pin 50 and holes 28 and 38. Pin 50 is thus secured in holes 28 and 38 by an interference fit between pin 50 and holes 28 and 38. Alternatively, adhesive may be used to secure pin 50 into holes 28 and 38. Flat sections 17 of superior surface 14 and inferior surface 16, and exterior surface 18 are then shaped into the proper desired form. Finally, teeth 12 are formed into superior surface 14 and inferior surface 16. In a preferred embodiment, the shaping of the parts and sections of implant 10 is performed by computer-controlled milling. However, alternative methods of forming the various parts of implant 10 may also be used.

Using the method of manufacture described above, teeth 12 are formed so that their tips are either at or below the planes defined by the surfaces of flat sections 17. In other alternative embodiments, teeth 12 may be formed so that they extend past the planes of flat sections 17 by first forming teeth 12 on superior surface 14 and inferior surface 16 before forming flat sections 17. Furthermore, by milling teeth 12 onto the superior surface 14 and inferior surface 16 of first part 20 before joining first part 20 with second part 30, teeth 12 may be formed only from cortical bone. However, this may increase the complexity of the manufacturing process.

In order to restore the intervertebral space to the proper size after the affected disc has been removed, implant 10 has a height, h, sized to match the height of the removed disc. Typically for discectomies, h is between about 5 mm to about 12 mm, but other heights may be used.

Implant 10 may also be configured for corpectomies. In which case, it should be noted that implants 10 can be configured so that h would be approximately 10 to approximately 150 mm. Other heights may also be used. These larger sizes could be used in corpectomy, a surgical procedure in which a section of several vertebrae is removed. Implants 10 would be inserted in the space created by the removed section of bone. Due to the nature of corpectomy, an accurate preoperative determination of the size of the implant needed is very difficult. Thus, implant 10 may be cut to the proper size by the surgeon. In such cases, the implants 10 preferably would only have teeth 12 on either superior surface 14 or inferior surface 16.

A threaded hole (not shown) may be formed on either anterior end 6, lateral surface 72, or medial surface 70 of implant 10 along exterior surface 18 to receive an inserter to implant the implant between the vertebrae. Alternatively, an instrument specifically configured to hold implant 10 by fitting snugly along at least portions of exterior surface 18, for example, at anterior end 6 and portions of medial surface 70 and lateral surface 72 of implant 10 may also be used. Other means for inserting implant 10 may be used in addition to or alternatively to the methods described above.

While the embodiments described above comprise parts formed from a single piece of cortical bone and single piece of cancellous bone, it will be appreciated that multiple pieces of cortical and/or cancellous bone may be used to form the parts of an implant in accordance with the present invention. It will also be appreciated that while the embodiments described above were formed from two parts joined together, an implant formed from more than two parts is also within the spirit and scope of the present invention.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

The invention claimed is:

1. An intervertebral implant for insertion between adjoining vertebra, said implant comprising:
    a three dimensional body including a superior surface sized and configured for contacting at least a portion of one of said adjacent vertebrae, and an inferior surface sized and configured for contacting at least a portion of said other of said adjacent vertebrae; said three dimensional body further comprising:
    a first part formed of cortical bone and a second part formed of cancellous bone, wherein said first and second parts are connected to one another, wherein substantially the entire superior and inferior surfaces of the first part comprises a plurality of teeth, and wherein at least one of said superior and inferior surfaces of said second part includes a first portion and a second portion, wherein said first portion includes a plurality of teeth and said second portion is substantially smooth, said toothed first portion of said second part defining a first surface area and said substantially smooth second portion of said second part defines a second surface area, said second surface area being greater than said first surface area;
    wherein said substantially smooth superior and inferior surfaces of said second portion of said second part define an upper plane and a lower plane, respectively, said plurality of teeth formed on said superior and inferior surfaces of said first part having a tip portion, said tip portion being sized and configured to be at or below said upper and lower planes; and
    wherein said first and second parts are connected by at least one dovetail joint, wherein said dovetail joint includes a male portion and a female portion, said male portion being receivable within said female portion, each of said first part and said second part further comprising at least one hole extending partially therethrough and receiving at least one pin to prevent said first part from moving with respect to said second part; at least one of said holes passes through said male and female portions of said dovetail joint so that at least one of said pins passes through said dovetail joint to secure said first and second parts to one another, wherein said male portion of said dovetail joint is on said first part and said female portion of said dovetail joint is on said second part.

2. The implant of claim 1, wherein said plurality of teeth formed on at least one of said superior and inferior surfaces of said first part are sized and configured to provide a mechanical interlock between said implant and said adjacent vertebra and said substantially smooth second portion of said second part is sized and configured to deform in order to conform to said adjacent vertebra.

3. The implant of claim 1, wherein both said superior and inferior surfaces of said second part includes a first portion and a second portion.

4. The implant of claim 1, further comprising a ledge formed on at least one of said superior and inferior surfaces of said second part, said ledge residing between said first and second portions.

5. The implant of claim 1, wherein said female portion of said second part has a first dimension and said male portion of said first part has a second dimension, said first dimension being smaller than said second dimension thus creating an interference fit between said male and female portions.

6. The implant of claim 1, wherein said pin has a first diameter and said at least one hole has a second diameter, said first diameter being larger than said second diameter so that an interference fit is created between said at least one pin and said at least one hole.

7. The implant of claim 1, further comprising a first adhesive for securing said at least one pin to said at least one hole.

8. The implant of claim 7, further comprising a second adhesive for securing said first part to second part.

9. The implant of claim 1, wherein said three dimensional body further includes a posterior end, an anterior end, and first and second side surfaces sized and configured to extend between said anterior end to said posterior end, wherein said first and second side surfaces of said first part are substantially parallel with respect to one another and wherein said first and second side surfaces of said second portion of said second part are angled in towards said posterior end at an angle.

10. An intervertebral implant for insertion between adjoining vertebra, said implant comprising:
    a three dimensional body including a superior surface sized and configured for contacting at least a portion of one of said adjacent vertebrae, and an inferior surface sized and configured for contacting at least a portion of said other of said adjacent vertebrae; said three dimensional body further comprising:
    a first part formed of bone and a second part formed of bone;
    wherein said first and second parts are connected to one another by at least one dovetail joint, wherein said dovetail joint includes a male portion and a female portion, said female portion being sized and configured to receive said male portion, each of said first part and said second parts further comprising at least one hole extending partially therethrough and receiving at least one pin to prevent said first part from moving with respect to said second part; at least one of said holes passes through said male and female portions of said dovetail joint so that at least one of said pins passes through said dovetail joint to secure said first and second parts to one another;
    wherein said first part is formed of cortical bone and said second part is formed of cancellous bone; said male portion of said dovetail joint is on said first part and said female portion of said dovetail joint is on said second part;
    wherein substantially the entire superior and inferior surfaces of the first part comprises a plurality of teeth, wherein said superior and inferior surfaces of said second part includes a first portion and a second portion, wherein said superior and inferior surfaces of said first portion of said second part include a plurality of teeth and said second portion of said second part is substantially smooth; said toothed first portion of said second part defines a first surface area and said substantially smooth second portion of said second part defines a second surface area, said second surface area being greater than said first surface area; and wherein said substantially smooth superior and inferior surfaces of said second portion of said second part define an upper plane and a lower plane, respectively, said plurality of teeth formed on said superior and inferior surfaces of said first part having a tip portion, said tip portion being sized and configured to be at or below said upper and lower planes.

11. The implant of claim 10, wherein said plurality of teeth formed on said superior and inferior surfaces of said first part are sized and configured to provide a mechanical interlock between said implant and said adjacent vertebra and said substantially smooth portions formed on said superior and inferior surfaces of said second portion of said second part are sized and configured to deform in order to conform to said adjacent vertebra.

12. The implant of claim 10, further comprising a ledge formed on at least one of said superior and inferior surfaces of said second part, said ledge residing between said first and second portions.

13. The implant of claim 10, wherein said three dimensional body further includes a posterior end, an anterior end, and first and second side surfaces sized and configured to extend between said anterior end to said posterior end, wherein said first and second side surfaces of said first part are substantially parallel with respect to one another and wherein said first and second side surfaces of said second portion of said second part are angled in towards said posterior end at an angle.

14. An intervertebral implant for insertion between adjoining vertebra, said implant comprising:

a three dimensional body including a superior surface sized and configured for contacting at least a portion of one of said adjacent vertebrae, and an inferior surface sized and configured for contacting at least a portion of said other of said adjacent vertebrae; said three dimensional body further comprising:

a first part formed of cortical bone and a second part formed of cancellous bone, wherein said first part is connected to said second part, wherein substantially the entire superior and inferior surfaces of the first part comprises a plurality of teeth and wherein said superior and inferior surfaces of said second part includes a first portion and a second portion, wherein said superior and inferior surfaces of said first portion of said second part include a plurality of teeth and said second portion of said second part is substantially smooth;

wherein said first and second parts are connected by a dovetail joint, wherein said dovetail joint includes a male portion and a female portion, said male portion being receivable with said female portion, each of said first part and said second parts further comprising a hole extending partially therethrough and receiving a pin to prevent said first part from moving with respect to said second part; said holes passing through said male and female portions of said dovetail joint so that at least one of said pins passes through said dovetail joint to secure said first and second parts to one another, wherein said male portion of said dovetail joint is on said first part and said female portion of said dovetail joint is on said second part; and wherein said substantially smooth superior and inferior surfaces of said second portion of said second part define an upper plane and a lower plane, respectively, said plurality of teeth formed on said superior and inferior surfaces of said first part having a tip portion, said tip portion being sized and configured to be at or below said upper and lower planes.

15. The implant of claim 14, wherein said toothed first portion of said second part defines a first surface area and said substantially smooth second portion of said second part defines a second surface area, said second surface area being greater than said first surface area.

16. The implant of claim 14, wherein said plurality of teeth formed on said superior and inferior surfaces of said first part are sized and configured to provide a mechanical interlock between said implant and said adjacent vertebra and said substantially smooth portions formed on said superior and inferior surfaces of said second portion of said second part are sized and configured to deform in order to conform to said adjacent vertebra.

17. The implant of claim 14, further comprising a ledge formed on at least one of said superior and inferior surfaces of said second part, said ledge residing between said first and second portions.

18. The implant of claim 14, wherein said three dimensional body further includes a posterior end, an anterior end, and first and second side surfaces sized and configured to extend between said anterior end to said posterior end, wherein said first and second side surfaces of said first part are substantially parallel with respect to one another, and wherein said first and second side surfaces of said second portion of said second part are angled in towards said posterior end at an angle.

* * * * *